United States Patent [19]

Thomas et al.

[11] 4,058,392

[45] Nov. 15, 1977

[54] TETRASUBSTITUTED UREA COMPOUNDS AND HERBICIDAL COMPOSITIONS

[75] Inventors: Rudolf Thomas; Wolfgang Krämer, both of Wuppertal; Ludwig Eue, Cologne; Carl Metzger; Gerhard Jäger, both of Wuppertal, all of Germany

[73] Assignee: Bayer Aktiengesellschaft, Leverkusen, Germany

[21] Appl. No.: 395,794

[22] Filed: Sept. 10, 1973

[30] Foreign Application Priority Data

Sept. 27, 1972 Germany .............................. 2247310

[51] Int. Cl.$^2$ ................. C07C 127/15; C07C 127/17; C07C 127/19
[52] U.S. Cl. ............................. 71/106; 260/553 A; 260/553 R; 560/251; 560/106; 560/228; 560/221; 560/62; 560/124; 560/123; 560/122; 560/1; 560/128; 71/88; 71/98; 71/100; 71/103; 71/107; 71/108; 71/110; 71/119; 71/120; 260/208 C; 260/455 B; 260/450 R; 544/159; 544/165
[58] Field of Search .............. 260/490, 468 R, 468 L, 260/489 R, 485 J, 486 R, 486 M, 487, 553 A; 71/106, 120

[56] References Cited

U.S. PATENT DOCUMENTS

| | | | |
|---|---|---|---|
| 3,808,262 | 4/1974 | Zeeh et al. ............................. | 260/971 |
| 3,847,971 | 11/1974 | Köenig et al. ......................... | 260/490 |
| 3,860,644 | 1/1975 | Krenzer et al. ....................... | 260/545 |

FOREIGN PATENT DOCUMENTS 227,400 10/1958 Australia .......................... 260/473 R

*Primary Examiner*—Robert Gerstl

*Attorney, Agent, or Firm*—Burgess, Dinklage & Sprung

[57] ABSTRACT

New N,N'-tetrasubstituted ureas of the formula

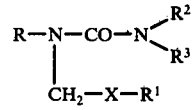

in which

X is oxygen, sulfur or an $NR^5$— or $SO_2$—group,

R is alkyl or an optionally substituted aryl group, or an optionally substituted aralkyl group, $R^1$ and $R^4$ are individually optionally substituted hydrocarbyl which may contain oxygen or sulfur, $R^2$ is optionally substituted alkyl, optionally substituted alkenyl, optionally substituted alkoxy or cycloalkyl, $R^3$ is alkyl, which may optionally be substituted by halogen, or is alkenyl, or $R^2$ and $R^3$ conjointly form an alkylene bridge, which can be interrupted by a hetero-atom, such as O, or N-alkyl group and which forms a heterocyclic ring with the adjoining nitrogen atom, $R^1$ and $R^5$, independently of one another, are each alkyl or conjointly form an alkylene bridge, which can be interrupted by a hetero-atom, such as O, and which forms a heterocyclic ring with the adjoining nitrogen atom; and Y is oxygen or sulfur; are remarkably effective and selective herbicides.

19 Claims, No Drawings

TETRASUBSTITUTED UREA COMPOUNDS AND HERBICIDAL COMPOSITIONS

The present invention relates to certain new N,N'-tetra-substituted urea compounds, to herbicidal compositions containing them and to their use as herbicides.

It is known that N,N'-trisubstituted ureas such as 3-(3,4-dichlorophenyl)-1,1-dimethylurea, 3-(4-chlorophenyl)-1,1-dimethylurea and 3-(4-chlorophenyl)-1-methyl-1methoxyurea possess herbicidal activity, from U.S. Pat. Nos. 2,655,444; 2,655,445; 2,655,447 and 2,655,534 and German Auslegeschrift (German published Specification) 1, 028,986. However, the activity of such compounds is so high that, even on application of low concentrations, they cannot be used in every case as selective herbicidal agents in various crops, for example in cotton, cereals and carrots.

The present invention provides, as new compounds, the N,N'-tetrasubstituted ureas of the formula

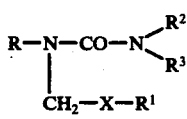

in which

X is oxygen, sulfur or an $NR^5$— or $SO_2$—group,

R is alkyl or an optionally substituted aryl group, or an optionally substituted aralkyl group, $R^1$ is alkyl, alkenyl, alkynyl, alkoxyalkyl, halogenoalkyl, halogenoalkenyl, halogenoalkynyl, cycloalkyl, cycloalkenyl or an optionally substituted aryl or aralkyl group, or, provided X is oxygen, the grouping —C(Y)-$R^4$, wherein Y is oxygen or sulfur;

$R^4$ is one of the radicals defined under $R^1$ above, hydrogen or alkyl substituted by an alkoxy, alkoxycarbonyl, aryloxy or aralkoxy radical;

$R^2$ is optionally substituted alkyl, optionally substituted alkenyl, optionally substituted alkoxy, or cycloalkyl;

$R^3$ is alkyl, which may optionally be substituted by halogen, or alkenyl; or $R^2$ and $R^3$ together form an alkylene bridge, which can be interrupted by a hetero-atom, such as oxygen or by an N-alkyl group, forming a heterocyclic ring with the adjoining nitrogen atom;

$R^1$ and $R^5$, independently of one another, are each alkyl or, together, represent an alkylene bridge, which can be interrupted by a hetero-atom, such as oxygen, forming a heterocyclic ring with the adjoining nitrogen atom.

The compounds (I) have been found to possess very good herbicidal properties.

Surprisingly, the tetrasubstituted ureas according to the invention are distinguished by both good herbicidal activity and substantially better selectively in crops such as cotton, cereals, carrots and beans than the prior-art trisubstitured ureas, such as 3-(3,4-dichlorophenyl)-1,1-dimethylurea, 3-(4-chlorophenyl)-1,1-dimethylurea and 3-(3,4-dichlorophenyl)-1-methyl-1-methoxyurea, which are chemically the nearest compounds of the same type of action. The compounds according to the invention thus represent an enrichment of the art.

Preferably, in the compounds of formula (I), R is straight-chain alkyl of from 1 to 4 carbon atoms or phenyl or benzyl, either of which may optionally be carrying one or more substituents, preferably selected from halogen (especially chlorine), straight-chain or branched alkyl of from 1 to 4 carbon atoms (especially methyl), halogenoalkyl of from 1 to 2 carbon atoms and 2 to 5 halogen atoms (especially fluorine, as in, for example, 2-(or 4-, or 5-) trifluoromethyl), alkoxy of from 1 to 4 carbon atoms, halogenoalkoxy of from 1 to 5 halogen atoms (especially fluorine, as in, for example, trifluoromethoxy), and phenoxy, which can be substituted by halogen (especially chlorine) or the nitro group; $R^2$ is straight-chain or branched alkyl of from 1 to 4 carbon atoms or alkenyl of from 2 to 6 carbon atoms, either of which can be substituted by alkoxy of from 1 to 3 carbon atoms, by halogenoalkyl of from 1 to 2 carbon atoms and 1 to 3 halogen atoms (especially chlorine) or by halogen (especially chlorine or bromine), or is alkoxy of from 1 to 4 carbon atoms (especially methoxy); $R^3$ is straight-chain or branched alkyl of from 1 to 4 carbon atoms, which can be mono-substituted or poly-substituted by halogen (especially chlorine), or is alkenyl of from 2 to 6 carbon atoms, or $R^2$ and $R^3$ conjointly form a straight-chain or branched alkylene bridge of from 3 to 8 members, which forms a heterocyclic ring with the adjoining nitrogen atom and which can be interrupted by a further heteroatom (such as O) or by an N-alkyl group of which the alkyl part is an aliphatic radical of from 1 to 3 carbon atoms (especially methyl); X is oxygen, sulfur, the $SO_2$ group or an $NR^5$ group, whereby $R^1$ and $R^5$, independently of one another, are each straight-chain or branched alkyl of from 1 to 4 carbon atoms or, $R^1$ and $R^5$ conjointly form an alkylene bridge which, together with the amine nitrogen, forms a five-membered to seven-membered heterocyclic ring, which can contain a further hetero-atom (particularly O); and $R^1$ is straight-chain or branched alkyl or halogenoalkyl of from 1 to 6 carbon atoms, the latter having 1 to 3 halogen atoms (especially fluorine or chlorine), straight-chain or branched alkenyl or halogenoalkenyl of from 2 to 6 carbon atoms, the latter having 1 to 4 halogen atoms (especially fluorine or chlorine), straight-chain or branched alkynyl or halogenoalkynyl of from 3 to 6 carbon atoms, the latter having 1 to 4 fluorine or chlorine atoms, phenyl or benzyl, either of which may be carrying one or more substituents, preferably selected from alkyl of from 1 to 4 carbon atoms (especially methyl or tertiary butyl) and halogen (especially chlorine), or cycloalkyl or cycloalkenyl of from, in either case, 3 to 8 carbon atoms, or, provided X is oxygen, $R^1$ is the grouping —C(Y)$R^4$, wherein $R^4$ is a radical stated above for $R^1$ or is hydrogen or substituted alkyl of from 1 to 2 carbon atoms, the preferred substituents being alkoxy or alkoxycarbonyl of from 1 to 3 carbon atoms in the alkyl moiety (for example methoxy or methoxycarbonyl), aryloxy of from 6 10 carbon atoms, or aralkoxy of from 6 to 10 carbon atoms in the aryl moiety and 1 to 2 carbon atoms in the alkyl moiety, the two last-mentioned radicals optionally carrying one or more substituents, preferably selected from alkyl of from 1 to 4 carbon atoms (especially methyl) and halogen (especially chlorine).

The present invention also provides a process for the preparation of an N,N'-tetrasubstituted urea of the formula (I) in which a. an N-halogenomethylurea of the formula

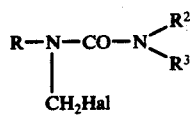 (II)

in which

R, R² and R³ have the above-mentioned meanings, and

Hal is halogen, preferably chlorine, is reacted with an alcohol, mercaptan, phenol, thiophenol, carboxylic acid, sulfinic acid or amine of the formula

 (III)

in which

X and R¹ have the above-mentioned meanings, in the presence of an acid-binding agent and optionally in the presence of a solvent, or (b) an N-halogenomethylurea of the formula (II) above is reacted with a compound of the formula

 (IV), in which

X and R¹ have the above-mentioned meanings, and

A is an optionally substituted ammonium cation,

Such as ammonium, alkylammonium or dialkylammonium, an alkali metal cation or an equivalent of an alkaline earth metal cation, in the presence of a solvent.

If 3-(4-trifluoromethylphenyl)-3-chloromethyl-1,1-dimethylurea and 2-chloroethanol are used as starting materials, the course of the reaction can be represented by the following equation:

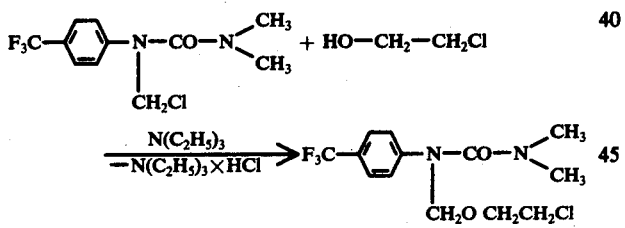

If 3-(3-chloro-4-methylphenyl)-3-chloromethyl-1,1-dimethylurea and isopropylmercaptan are used as starting materials, the course of the reaction can be represented by the following equation:

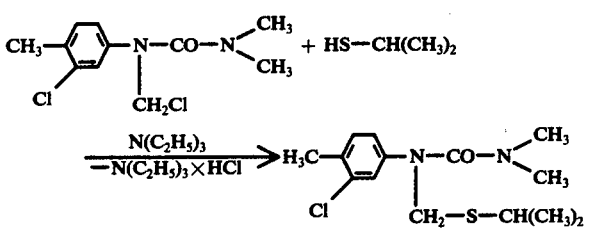

If 3-(4-chlorophenyl)-3-chloromethyl-1,1-dimethylurea and morpholine are used as starting materials, the course of the reaction can be represented by the following equation:

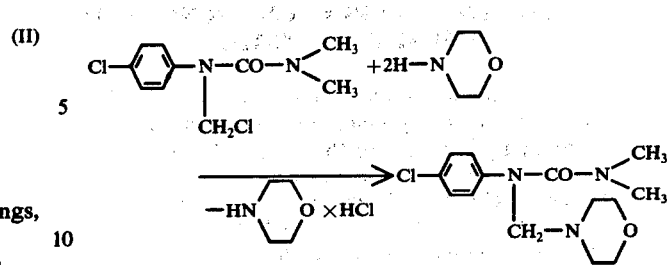

If 3-(4-chlorophenyl)-3-chloromethyl-1,1-dimethylurea and sodium pivalate are used as starting materials, the course of the reaction can be represented by the following equation:

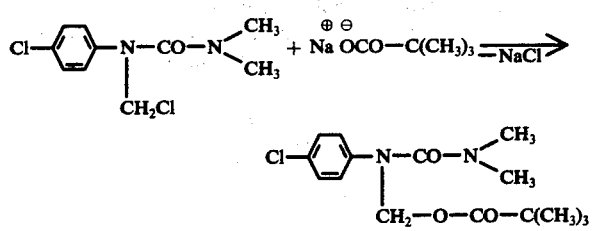

The following may be listed as examples of the N-halogenomethylureas (II) which can be used according to the invention: 3-phenyl-3-chloromethyl-1,1-dimethylurea, 3-butyl-3-chloromethyl-1,1-dimethylurea, 3-benzyl-3-chloromethyl-1,1-dimethylurea, 3-[4-(chlorophenoxy)-phenyl]-3-chloromethyl-1,1-dimethylurea, 3-(3-chloro-4-methoxyphenyl)-3-chloromethyl-1,1-dimethylurea, 3-(3-chloro-4-methylphenyl)-3-chloromethyl-1,1dimethylurea, 3-(3-chloro-4-trifluoromethylphenyl)-3-chloromethyl-1,1-dimethylurea, 3-(3-chloro-4-trifluoromethoxyphenyl)-3-chloromethyl-1,1-dimethylurea, 3-(4-ethoxyphenyl)-3-chloromethyl-1,1-dimethylurea, 3-(3-methylphenyl)-3-chloromethyl-1,1-dimethylurea, 3-(3,4-dichlorophenyl)-3-chloromethyl-1-methyl-1-butylurea, 3-(4-chloro-3-nitrophenyl)-3-chloromethyl-1,1-dimethylurea, 3-(4-chlorophenyl)-3-chloromethyl-1,1-dimethylurea, 3-(4-chlorophenyl)-3-chloromethyl-1,1-dipropen-(3)-yl-urea, 3-(3,4-dichlorophenyl)-3-chloromethyl-2,2-dipropen-(3)-yl-urea, 3-(4-chlorobenzyl)-3-chloromethyl-1,1-dimethylurea, 3-(3,4-dichlorophenyl)-3-chloromethyl-1-methyl-1-methoxyurea, 3-(4-chlorophenyl)-3-chloromethyl-1-methyl-1-methoxyurea, 3-(3,4-dichlorophenyl)-3chloromethyl-1-morpholinourea, 3-(3,4-dichlorophenyl)-3-chloromethyl-1-(4-methyl-piperazinyl)-urea, 3-(3,4-dichlorophenyl)-3-chloromethyl-1,1-dimethylurea, 3-(4-chlorophenyl)-3-chloromethyl-1,1-di-n-butylurea, 3-(4-trifluoromethylphenyl)-3-chloromethyl-1,1-dimethylurea, 3-(4-chloro-3-trifluoromethylphenyl-3-chloromethyl-1,1-dimethylurea and 3-(4-methylphenyl)-3-chloromethyl-1,1-dimethylurea.

The N-halogenomethylureas of the formula (II) have not previously been described in the literature but can be prepared by reacting an N,N'-trisubstituted urea of the general formula

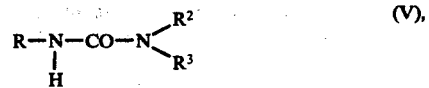 (V), in which

R, $R^2$ and $R^3$ have the above-mentioned meanings, with at least an equimolar amount of formaldehyde (which may be formed in situ from a formaldehyde donor) and a halogenating agent at temperatures of from $-10°$ to about $+150°$ C, optionally in the presence of a diluent and a hydrogen halide or a Lewis acid as a catalyst. This process forms the subject of German Patent Application P 22 10 603. The N,N'trisubstituted ureas of the formula (V) are in most cases known; those which have not yet been described in the literature can be prepared according to known processes (see, for example, Z. Angewandte Chemie 75, 851–854 (1963).

A in the formula (IV) is preferably an ammonium or a substituted ammonium cation, preferably substituted by alkyl of from 1 to 4 carbon atoms in the straight-chain or branched alkyl radical, or an alkali metal cation, such as a sodium or potassium ion, or an alkaline earth metal cation, such as a magnesium or calcium ion (or, more precisely, one equivalent thereof)

The following may be mentioned as examples of the alcohols, mercaptans, phenols, thiophenols, carboxylic acids, sulphinic acids and amines (III), as well as their salts (IV), which can be used according to this invention: methanol, ethanol, propanol, isopropanol, tertiary butanol, secondary butanol, allyl alcohol, propargyl alcohol, vinyl alcohol, 1-methyl-propyn-(3) -ol, 1,1-dimethyl-propyn-(3)-ol,1,1-dimethyl-propen-(3)-ol, 1-methyl-propen-(3)-ol, propen-(3)-ol, 2-chloroethanol; benzyl alcohol, cyclohexanol, 4-chloro-2-butynol, ethylene glycol monomethyl ether, 2,3,6-trichlorobenzyl alcohol, buten-(3)-ol, 1-methyl-butyl-(3)-ol; phenol, 2,4-dichlorophenol, 4-chloro-2-methyl-phenol, 4-chlorophenol, 2,4-dinitrophenol; methylmercaptan, ethylmercaptan, propylmercaptan, isopropylmercaptan, butylmercaptan, secondary butylmercaptan, isobutylmercaptan; propene-(3)-mercaptan, benzylmercaptan; 4-chlorothiophenol, thiophenol, 4-chloro-2-methyl-thiophenol; dimethylamine, morpholine, piperidine, 3,4-dichloroaniline; sodium acetate, sodium monochloroacetate, sodium dichloroacetate; sodium trichloroacetate, sodium trifluoroacetate; propionic acid, 3-chloropropionic acid, 2-chloropropionic acid, 2,2-dichloropropionic acid, 2,2-dimethylpropionic acid, butyric acid, 2-methylbutyric acid, isobutyric acid, 2-chloro-3,3-dimethylbutyric acid; valeric acid, 2-methylvaleric acid, 3-methylvaleric acid, isovaleric acid; myristic acid, palmitic acid, lauric acid, stearic acid, lavulinic acid, succinic acid monomethyl ester, 2-ethylcaproic acid, but-2-ene-1-carboxylic acid, prop-2-ene-1-carboxylic acid, non-8-ene-1-carboxylic acid, lactic acid, cyclopropanecarboxylic acid, cyclohexanecarboxylic acid, cyclohexene-1-carboxylic acid, benzoic acid, 4-chlorobenzoic acid, 4-tertiary butylbenzoic acid, phenylacetic acid, 4-chlorophenoxyacetic acid, 1-chloro-2-(4-chlorophenyl)-2-methyl-propionic acid, thioacetic acid, potassium xanthate, sodium 4-chlorobenzenesulphinate, sodium isobutyrate, sodium fluoroacetate, sodium crotonate and formic acid.

The alcohols, mercaptans, phenols, thiophenols, carboxylic acids, thiocarboxylic acids, sulphinic acids and amines (III) as well as their salts (IV), which are used as starting materials, are known.

All inert organic solvents can be used as diluents in the process variant (a) according to the invention, especially hydrocarbons such as ligroin, benzine, benzene and toluene; halogenohydrocarbons, such as dichloromethane, chloroform and carbon tetrachloride; ethers such as diethyl ether, dioxane or tetrahydrofuran; and esters such as ethyl acetoacetate and ethyl acetate.

All customary acid-acceptors can be used as the acid-binding agent, especially alkali metal hydroxides, alkali metal carbonates and tertiary organic bases. Sodium carbonate, triethylamine and pyridine may be mentioned as being particularly suitable.

The reaction temperatures can be varied within a fairly wide range. In general, the reaction in variant (a) is carried out at from $-20°$ C to $+100°$ C, preferably from $-10°$ C to $+80°$ C.

In carrying out process variant (a), 1 mole of the compound of the formula (III) and 1 to 1.2 moles of acid-binding agent are employed per mole of N-halogenomethylurea of the formula (II). Further deviation from the stoichiometric ratio produces no significant improvement in yield.

To isolate the compounds of the formula (I), the precipitate formed is filtered off and well washed and the resulting combined filtrates are freed of the solvent in vacuo. It is also possible to evaporate the reaction mixture to dryness without filtering off the precipitate, to take up the residue with water and extract with chlorinated hydrocarbons, and to dry the organic phase and distil off the solvents. The residue is treated further according to customary methods and may be purified by recrystallisation. However, in some cases oils are obtained which can neither be made to crystallise nor be distilled without decomposition.

All polar organic solvents can be used as diluents in the process variant (b) according to the invention, especially nitriles, such as acetonitrile and tolunitrile, sulphoxides, such as dimethylsulphoxide, or amides such as dimethylformamide.

The reaction temperatures can also be varied over a fairly wide range. In general, the reaction in variant (b) is carried out at from $0°$ C to $150°$ C, preferably from $20°$ C to $100°$ C.

In carrying out the process according to variant (b), 1 to 2 moles of the compound of the formula (IV) are employed per mole of the compound of the formula (II).

To isolate the compounds of the formula (I), the halide produced is filtered off, the filtrate is evaporated to dryness and the residue is taken up in an organic solvent. After brief shaking with water, the organic phase is dried and thereafter the solvent is distilled off in vacuo. The product thus obtained is pure in many cases but can, if necessary, be purified further according to customary methods.

The preparation of the compounds of this invention is illustrated in the following Examples:

EXAMPLE 1

Preparation of 3-(4-trifluoromethylphenyl)-3-(2-chloroethoxymethyl)-1,1-dimethylurea 25 g (0.09 mole of 3-(4-trifluoromethylphenyl)-3-chloromethyl-1,1,-dimethylurea were dissolved in 200 ml of anhydrous carbon tetrachloride. A solution of 8 g (0.1 mole) of 2-chloroethanol and 10.1 g (0.1 mole) of triethylamine in 50 ml of anhydrous carbon tetrachloride was added dropwise thereto, while stirring. While doing so, the temperature rose from room temperature to 43° C and slowly returned to its initial value after the exothermic reaction had subsided. After stirring for a further hour at room temperature, the solvent of the resulting suspension was distilled off in vacuo, the residue was taken up in 100 ml of water and the aqueous suspension was extracted by shaking two or three times with 100 ml of carbon tetrachloride at a time. The combined carbon tetrachloride phases were dried over sodium sulfate and the solvent was distilled off.

26 g (90% of theory) of 3-(4-trifluoromethylphenyl)-3-(2-chloroethoxy-methyl)-1,1-dimethylurea were obtained as an oil which slowly solidified to crystals which had a melting point of 39° C.

EXAMPLE 2

Preparation of
3-phenyl-3-methoxy-methyl-1,1-dimethylurea

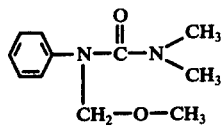

(Compound 2)

A solution of 3.3 g (0.1 mole) of methanol and 10.1 g (0.1 mole) of triethylamine were added dropwise to a solution of 23 g (0.1 mole) of 3-phenyl-3-chloromethyl-1,1-dimethylurea in 125 ml of ethyl acetate, while stirring and cooling externally, is such a way that the reaction temperature did not exceed 20° C. After stirring for one hour at room temperature, the precipitate so produced was filtered off and well washed with about 50 ml of ethyl acetate. The combined filtrates and wash solutions were freed of the solvent in vacuo and the resulting oil was taken up in 100 ml of benzene and twice washed with 50 ml of water at a time. The organic phase was dried over sodium sulfate and the solvent was distilled off. The oily residue was taken up in 100 ml of benzene and twice washed with 50 ml of water at a time. The organic phase was dried over sodium sulfate and the solvent was distilled off. The oily residue was taken up in 100 ml of a 1:1 mixture of ether and petroleum ether, the solution was filtered and the solvent of the filtrate was distilled off in vacuo. 17.5 g (84% of theory) of 3-phenyl-3-methoxy-methyl-1,1-dimethylurea were left as an oil.

The compound was best characterized by its proton resonance spectrum (PMR):

The chemical shift of the CH$_2$ group of the compound

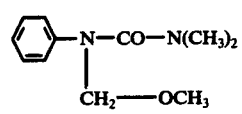

(2a), measured at 60 MHz in carbon tetrachloride as the solvent and against tetramethylsilane (TMS) as the internal standard ($\delta$ = 0 ppm), was 4.95 ppm.

EXAMPLE 3

Preparation of
3-(4-Chlorophenyl)-3-n-butylthiomethyl-1-methyl-1-methoxyurea

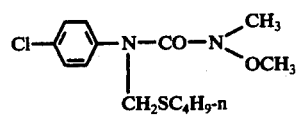

(Compound 3)

11.75 g (0.05 mole) of 3-(4-chlorophenyl)-3-chloromethyl-1-methyl-1-methoxy-urea were dissolved in 125 ml of ethyl acetate. To the solution, cooled to 10° C, was added dropwise, while stirring and cooling externally, a solution of 4.5 g (0.05 mole) of n-butylmercaptan and 5.05 g (0.05 mole) of triethylamine in 50 ml of ethyl acetate in such a way that the internal temperature did not exceed 20° C. The mixture was stirred overnight at room temperature, the resulting precipitate was subsequently filtered off and rinsed with 50 ml of ethyl acetate, and the filtrate was freed of the solvent in vacuo.

3-(4-Chlorophenyl)-3-n-butylthiomethyl-1-methyl-1-methoxyurea was obtained as an oil, in quantitative yield. $\delta_{CH_2}$ = 4.80 ppm (measured at 60 MHz, in CDCl$_3$, against TMS as the internal standard).

EXAMPLE 4

Preparation of
3-(4-chlorophenyl)-3-(4'-morpholinomethyl)-1,1-dimethylurea

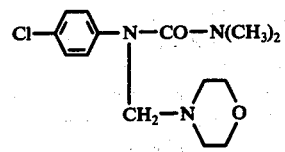

(Compound 4)

24.7 g (0.1 mole) of 3-(4-chlorophenyl)-3-chloromethyl-1,1-dimethylurea were dissolved in 100 ml of carbon tetrachloride and a solution of 8.7 g (0.1 mole) of morpholine and 10.1 g (0.1 mole) of triethylamine in 100 ml of ethyl acetate was added dropwise thereto, while stirring and cooling externally, so that the internal temperature did not exceed 0° C. After stirring for two hours at room temperature, the precipitate was filtered off and well rinsed with ethyl acetate, and the filtrate was freed of the solvent in vacuo. The resulting residue was recrystallized from a 1:1 mixture of ether and petroleum ether.

13.9 g (43% of theory) of 3-(4-chlorophenyl)-3-(4'-morpholinomethyl)-1,1-dimethylurea of melting point 89°-92° C were obtained.

EXAMPLE 5

Preparation of
3-(4-chlorophenyl)-3-tert.-butylcarboxymethyl-1,1-dimethylurea

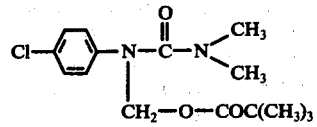

(Compound 5)

24.7 g (0.1 mole) of 3-(4-chlorophenyl)-3-chloromethyl-1,1-dimethylurea were dissolved in 200 ml of a mixture of equal parts of anhydrous benzene and ethyl acetate. A solution of 10.2 g (0.1 mole) of pivalic acid and 10.1 g (0.1 mole) of triethylamine in 50 ml of anhydrous benzene was added dropwise to the first solution, while stirring and cooling externally, in such a way that the internal temperature did not exceed 20° C. After stirring for one hour at room temperature, the resulting precipitate of triethylammonium chloride was filtered off and well washed with 50 ml of ethyl acetate. The filtrate was freed of the solvent in vacuo and the resulting residue was recrystallized from ligroin.

16 g (51% of theory) of 3-(4-chlorophenyl)-3-tert.-butylcarboxymethyl-1,1-dimethylurea of melting point 90°-95° C were obtained.

EXAMPLE 6

Preparation of 3-(3-chloro-4-trifluoromethoxyphenyl)-3-(4-chlorophenyl-1-carboxymethyl)-1,1-dimethylurea

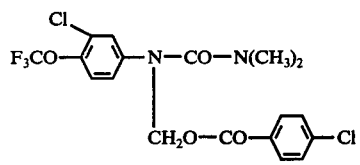

(Compound 6)

A solution of 33.1 g (0.1 mole) of 3-(3-chloro-4-trifluoromethoxyphenyl)-3-chloromethyl-1,1-dimethylurea in 100 ml of anhydrous acetonitrile was added dropwise to a suspension of 27 g (0.15 mole) of sodium 4-chlorobenzoate in 300 ml of anhydrous acetonitrile, in the course of which the temperature of the solution rose to 30°-35° C. The mixture was stirred for one hour at room temperature, the precipitate was filtered off, and the solvent of the filtrate was distilled off under reduced pressure. The oil which remained slowly crystallized throughout.

41 g (91% of theory) of 3-(3-chloro-4-trifluoromethoxyphenyl)-3-(4-chlorophenyl-1-carboxymethyl)-1,1-dimethylurea of melting point 77° C were obtained.

The compounds listed in Table 1 which follows were prepared by methods analogous to those described in Examples 1 to 6:

TABLE 1

$$R-N-CO-N \begin{matrix} R^2 \\ R^3 \end{matrix} \quad (I)$$
$$| \\ CH_2-X-R^1$$

| Example No. | R | $R^1$ | $R^2$ | $R^3$ | X | Melting point [° C]; Refractive index $[n_D^{20}]$ | $\delta_{CH_2}$ (ppm) at 60 MHz TMS as internal standard (solvent) |
|---|---|---|---|---|---|---|---|
| 7 | 3,4-Cl₂-C₆H₃- | CH₃ | CH₃ | CH₃ | O | Oil | 4.99 (CDCl₃) |
| 8 | 3,4-Cl₂-C₆H₃- | CH(CH₃)₂ | CH₃ | CH₃ | O | Oil | 5.06 (CDCl₃) |
| 9 | 3,4-Cl₂-C₆H₃- | CH(CH₃)₂ | CH₃ | CH₃ | S | Oil | 4.82 (CDCl₃) |
| 10 | 3,4-Cl₂-C₆H₃- | CH₂CH₂Cl | CH₃ | CH₃ | O | Oil | 5.15 (CDCl₃) |
| 11 | 3,4-Cl₂-C₆H₃- | C₄H₉—n | CH₃ | CH₃ | S | Oil; 1,5542 | 4.81 (CDCl₃) |
| 12 | 3,4-Cl₂-C₆H₃- | CH₂C≡CH | CH₃ | CH₃ | O | 65 | 5.18 (CDCl₃) |
| 13 | 3,4-Cl₂-C₆H₃- | (CH₃)₂C—C≡CH | CH₃ | CH₃ | O | 112 | 5.24 (CDCl₃) |
| 14 | 3,4-Cl₂-C₆H₃- | CO—H | CH₃ | CH₃ | O | Oil | 5.77 (CDCl₃) |
| 15 | 3,4-Cl₂-C₆H₃- | CO—CH₃ | CH₃ | CH₃ | O | Oil | 5.63 (CDCl₃) |
| 16 | 3,4-Cl₂-C₆H₃- | CO—CH₂Cl | CH₃ | CH₃ | O | Oil | 5.72 (CDCl₃) |
| 17 | 3,4-Cl₂-C₆H₃- | CO—C(CH₃)₃ | CH₃ | CH₃ | O | 78 | 5.63 (CDCl₃) |
| 18 | 3,4-Cl₂-C₆H₃- | 3,4-Cl₂-C₆H₃- | CH₃ | CH₃ | O | Oil; 1,5833 | 5.67 (CDCl₃) |
| 19 | 3,4-Cl₂-C₆H₃- | C₆H₅—CH₂— | CH₃ | CH₃ | S | 86 | 4.67 (CDCl₃) |
| 20 | 3,4-Cl₂-C₆H₃- | 4-Cl-C₆H₄- | CH₃ | CH₃ | S | 77 | 5.08 (CDCl₃) |

TABLE 1-continued $$R-N-CO-N\begin{matrix}R^2\\R^3\end{matrix} \quad (I)$$
$$\underset{CH_2-X-R^1}{|}$$

| Example No. | R | R¹ | R² | R³ | X | Melting point [° C]; Refractive index [$n_D^{20}$] | $\delta_{CH_2}$ (ppm) at 60 MHz TMS as internal standard (solvent) |
|---|---|---|---|---|---|---|---|
| 21 | 2,4-Cl₂-C₆H₃- | 2,4-(CH₃,Cl)-C₆H₃- | CH₃ | CH₃ | O | Oil; 1.5802 | 5.54 (CDCl₃) |
| 22 | 2,4-Cl₂-C₆H₃- | -C(CH₃)₂-C≡CH | C₄H₉-n | CH₃ | O | Oil; 1.5316 | 5.19 (CDCl₃) |
| 23 | 2,4-Cl₂-C₆H₃- | CO-C₆H₄-Cl | C₄H₉ | CH₃ | O | Oil; 1.5605 | 5.88 (CDCl₃) |
| 24 | 2,4-Cl₂-C₆H₃- | CH(CH₃)₂ | OCH₃ | CH₃ | O | Oil | 5.09 (CDCl₃) |
| 25 | 2,4-Cl₂-C₆H₃- | C₄H₉-n | OCH₃ | CH₃ | S | Oil | 4.88 (CDCl₃) |
| 26 | 2,4-Cl₂-C₆H₃- | COCH₃ | OCH₃ | CH₃ | O | 68–70 | 5.61 (CDCl₃) |
| 27 | 2,4-Cl₂-C₆H₃- | COC(CH₃)₃ | OCH₃ | CH₃ | O | Oil | 5.60 (CDCl₃) |
| 28 | 2,4-Cl₂-C₆H₃- | CH₃ | CH₃ | CH₃ | S | Oil | 4.75 (CCl₄) |
| 29 | 4-Cl-C₆H₄- | CO-CH₃ | CH₃ | CH₃ | O | Oil | 5.54 (CDCl₃) |
| 30 | 4-Cl-C₆H₄- | C₆H₅-CH₂- | CH₃ | CH₃ | S | Oil | 4.70 (CDCl₃) |
| 31 | 4-Cl-C₆H₄- | CO-CH(CH₃)₂ | CH₃ | CH₃ | O | 80 | |
| 32 | 4-Cl-C₆H₄- | CH(CH₃)₂ | OCH₃ | CH₃ | O | Oil | 5.04 (CDCl₃) |
| 33 | 4-Cl-C₆H₄- | C₄H₉-n | CH₃ | CH₃ | S | Oil | 4.79 (CDCl₃) |
| 34 | 4-Cl-C₆H₄- | CO-CH₃ | OCH₃ | CH₃ | O | Oil | 5.77 (CDCl₃) |
| 35 | 4-Cl-C₆H₄- | CO-C(CH₃)₃ | OCH₃ | CH₃ | O | Oil | 5.33 (CDCl₃) |
| 36 | C₆H₅- | C₄H₉-n | CH₃ | CH₃ | S | Oil | 4.79 (CCl₄) |
| 37 | C₆H₅- | C(CH₃)₃ | CH₃ | CH₃ | O | Oil | 5.08 (CCl₄) |
| 38 | C₆H₅- | CO-CH₃ | CH₃ | CH₃ | O | Oil | 5.56 (CCl₄) |
| 39 | C₆H₅- | CO-CH(CH₃)₂ | CH₃ | CH₃ | O | Oil | 5.57 (CCl₄) |
| 40 | C₆H₅- | CO-C(CH₃)₃ | CH₃ | CH₃ | O | Oil | 5.55 (CCl₄) |
| 41 | C₆H₅- | CO-CH=CH₂ | CH₃ | CH₃ | O | Oil | 5.65 (CDCl₃) |
| 42 | C₆H₅- | CH(CH₃)₂ | CH₃ | CH₃ | O | Oil | 5.02 (CCl₄) |
| 43 | 4-Cl-C₆H₄- | 4-Cl-C₆H₄- | CH₃ | CH₃ | S | 76–81 | 5.02 (CDCl₃) |

TABLE 1-continued $$R-N(-CO-N\begin{smallmatrix}R^2\\R^3\end{smallmatrix})-CH_2-X-R^1 \quad (I)$$

| Example No. | R | R¹ | R² | R³ | X | Melting point [° C]; Refractive index [$n_D^{20}$] | $\delta_{CH_2}$ (ppm) at 60 MHz TMS as internal standard (solvent) |
|---|---|---|---|---|---|---|---|
| 44 | Cl—C₆H₄— | 2-CH₃, 4-Cl-C₆H₃— | CH₃ | CH₃ | O | Oil | 5.58 (CDCl₃) |
| 45 | Cl—C₆H₄— | 2-Cl, 4-Cl-C₆H₃— | CH₃ | CH₃ | O | Oil | 5.63 (CDCl₃) |
| 46 | 2,4-Cl₂-C₆H₃— | C₄H₉—n | morpholino | | S | Oil | 4.80 (CDCl₃) |
| 47 | 2,4-Cl₂-C₆H₃— | CO—C(CH₃)₃ | morpholino | | O | Oil | 5.63 (CDCl₃) |
| 48 | 2,4-Cl₂-C₆H₃— | C₆H₅— | morpholino | | S | 94–95 | 5.15 (CDCl₃) |
| 49 | CH₃—C₆H₄— | C₄H₉—n | CH₃ | CH₃ | S | Oil | 4.80 (CDCl₃) |
| 50 | CH₃—C₆H₄— | CO—C(CH₃)₃ | CH₃ | CH₃ | O | Oil | 5.61 (CDCl₃) |
| 51 | CH₃—C₆H₄— | C₆H₅— | CH₃ | CH₃ | S | Oil | 5.01 (CDCl₃) |
| 52 | F₃C—C₆H₄— | CH₃ | CH₃ | CH₃ | O | Oil; 1.4882 | 5.07 (CDCl₃) |
| 53 | F₃C—C₆H₄— | CH(CH₃)₂ | CH₃ | CH₃ | O | Oil; 1.4798 | 5.19 (CDCl₃) |
| 54 | F₃C—C₆H₄— | CH(CH₃)₂ | CH₃ | CH₃ | S | Oil; 1.5075 | 4.92 (CDCl₃) |
| 55 | F₃C—C₆H₄— | C₄H₉ | CH₃ | CH₃ | S | Oil; 1.5053 | 4.89 (CDCl₃) |
| 56 | F₃C—C₆H₄— | CH₂CH₂Cl | CH₃ | CH₃ | O | 39 | 5.17 (CDCl₃) |
| 57 | F₃C—C₆H₄— | C(CH₃)₃ | CH₃ | CH₃ | O | Oil; 1.4800 | 5.15 (CDCl₃) |
| 58 | F₃C—C₆H₄— | CH₂—C≡CH | CH₃ | CH₃ | O | 60 | 5.18 (CDCl₃) |
| 59 | F₃C—C₆H₄— | CO—CH₃ | CH₃ | CH₃ | O | 69 | 5.73 (CDCl₃) |
| 60 | F₃C—C₆H₄— | CO—C(CH₃)₃ | CH₃ | CH₃ | O | 66 | 5.69 (CDCl₃) |
| 61 | F₃C—C₆H₄— | Cl—C₆H₄— | CH₃ | CH₃ | S | Oil; 1.5628 | 5.18 (CDCl₃) |
| 62 | F₃C—C₆H₄— | 2-CH₃, 4-Cl-C₆H₃— | CH₃ | CH₃ | O | Oil; 1.5414 | 5.71 (CDCl₃) |
| 63 | F₃C—C₆H₄— | C₆H₅—CH₂— | CH₃ | CH₃ | S | Oil; 1.5541 | 4.89 (CDCl₃) |
| 64 | C₂H₅O—C₆H₄— | CH(CH₃)₂ | CH₃ | CH₃ | O | Oil | 5.07 (CDCl₃) |
| 65 | C₂H₅O—C₆H₄— | C₄H₉—n | CH₃ | CH₃ | S | Oil | 4.78 (CDCl₃) |

TABLE 1-continued $$R-N-CO-N{\overset{R^2}{\underset{R^3}{}}} \quad (I)$$
$$\phantom{R-N-CO-}|$$
$$\phantom{R-N-CO-N}CH_2-X-R^1$$

| Example No. | R | R¹ | R² | R³ | X | Melting point [° C]; Refractive index [$n_D^{20}$] | $\delta_{CH_2}$ (ppm) at 60 MHz TMS as internal standard (solvent) |
|---|---|---|---|---|---|---|---|
| 66 | 4-C₂H₅O-C₆H₄- | C₆H₄-CH₃ | CH₃ | CH₃ | S | Oil | 5.08 (CDCl₃) |
| 67 | 4-C₂H₅O-C₆H₄- | COC(CH₃)₃ | CH₃ | CH₃ | O | Oil | 5.63 (CDCl₃) |
| 68 | 3-Cl-4-F₃C-C₆H₃- | C₂H₅ | CH₃ | CH₃ | O | Oil | 5.08 (CDCl₃) |
| 69 | 3-Cl-4-F₃C-C₆H₃- | C₂H₅ | CH₃ | CH₃ | S | Oil; 1.5299 | 4.90 (CDCl₃) |
| 70 | 3-Cl-4-F₃C-C₆H₃- | CH(CH₃)₂ | CH₃ | CH₃ | O | Oil; 1.5005 | 5.18 (CDCl₃) |
| 71 | 3-Cl-4-F₃C-C₆H₃- | C(CH₃)₂CH=CH₂ | CH₃ | CH₃ | O | Oil; 1.5049 | 5.02 (CDCl₃) |
| 72 | 3-Cl-4-F₃C-C₆H₃- | CH(CH₃)—C≡CH | CH₃ | CH₃ | O | 70 | 5.22 (CDCl₃) |
| 73 | 3-Cl-4-F₃C-C₆H₃- | 4-Cl-2-CH₃-C₆H₃- | CH₃ | CH₃ | O | Oil; 1.5402 | 5.60 (CDCl₃) |
| 74 | 3-Cl-4-F₃C-C₆H₃- | COC₂H₅ | CH₃ | CH₃ | O | Oil; 1.5009 | 5.66 (CDCl₃) |
| 75 | 3-Cl-4-F₃C-C₆H₃- | COCHClCH₃ | CH₃ | CH₃ | O | Oil; 1.5060 | 5.73 (CDCl₃) |
| 76 | 3-Cl-4-F₃C-C₆H₃- | CO-C₆H₄-Cl | CH₃ | CH₃ | O | 125 | 5.88 (CDCl₃) |
| 77 | 3-Cl-4-F₃C-C₆H₃- | CO-CH₂-O-(2,4-Cl₂-C₆H₃) | CH₃ | CH₃ | O | 123 | 5.75 (CDCl₃) |
| 78 | 3-Cl-4-F₃CO-C₆H₃- | CO-CH(CH₃)₂ | CH₃ | CH₃ | O | Oil; 1.4801 | 5.72 (CDCl₃) |
| 79 | 3-Cl-4-CF₃O-C₆H₃- | CH(CH₃)₂ | CH₃ | CH₃ | O | Oil, 1.4841 | 5.11 (CDCl₃) |
| 80 | 3-Cl-4-CF₃O-C₆H₃- | C(CH₃)₂C≡CH | CH₃ | CH₃ | O | 80 | 5.21 (CDCl₃) |
| 81 | 3-Cl-4-CF₃O-C₆H₃- | 4-Cl-2-CH₃-C₆H₃- | CH₃ | CH₃ | O | Oil; 1.5289 | 5.56 (CDCl₃) |
| 82 | 3-Cl-4-CF₃O-C₆H₃- | CO-C₆H₄-Cl | CH₃ | CH₃ | O | 70 | 5.84 (CDCl₃) |
| 83 | 3-Cl-4-H₃C-C₆H₃- | CH₃ | CH₃ | CH₃ | O | Oil | 4.97 (CDCl₃) |
| 84 | 3-Cl-4-H₃C-C₆H₃- | CH(CH₃)₂ | CH₃ | CH₃ | O | Oil | 5.08 (CDCl₃) |
| 85 | 3-Cl-4-H₃C-C₆H₃- | CH(CH₃)₂ | CH₃ | CH₃ | S | 67 | 4.80 (CDCl₃) |
| 86 | 3-Cl-4-H₃C-C₆H₃- | CH₂CH₂Cl | CH₃ | CH₃ | O | Oil | 5.09 (CDCl₃) |

TABLE 1-continued $$R-N(CH_2-X-R^1)-CO-N(R^2)(R^3) \quad (I)$$

| Example No. | R | R¹ | R² | R³ | X | Melting point [°C]; Refractive index [$n_D^{20}$] | $\delta_{CH_2}$ (ppm) at 60 MHz TMS as internal standard (solvent) |
|---|---|---|---|---|---|---|---|
| 87 | 3-Cl-4-CH₃-C₆H₃— | COH | CH₃ | CH₃ | O | Oil | 5.70 (CDCl₃) |
| 88 | 3-Cl-4-CH₃-C₆H₃— | COCH₃ | CH₃ | CH₃ | O | Oil | 5.62 (CDCl₃) |
| 89 | 3-Cl-4-CH₃-C₆H₃— | COCH₂Cl | CH₃ | CH₃ | O | Oil | 5.72 (CDCl₃) |
| 90 | 3-Cl-4-CH₃-C₆H₃— | COC(CH₃)₃ | CH₃ | CH₃ | O | 57 | 5.64 (CDCl₃) |
| 91 | 3-Cl-4-H₃CO-C₆H₃— | CH₃ | CH₃ | CH₃ | O | Oil | 4.98 (CDCl₃) |
| 92 | 3-Cl-4-H₃CO-C₆H₃— | CH(CH₃)₂ | CH₃ | CH₃ | O | Oil | 5.04 (CDCl₃) |
| 93 | 3-Cl-4-CH₃O-C₆H₃— | CH(CH₃)₂ | CH₃ | CH₃ | S | 75 | 4.78 (CDCl₃) |
| 94 | 3-Cl-4-CH₃O-C₆H₃— | CH₂CH₂Cl | CH₃ | CH₃ | O | 84 | 5.11 (CDCl₃) |
| 95 | 3-Cl-4-CH₃O-C₆H₃— | COH | CH₃ | CH₃ | O | Oil | 5.67 (CDCl₃) |
| 96 | 3-Cl-4-CH₃O-C₆H₃— | COCH₃ | CH₃ | CH₃ | O | Oil | 5.59 (CDCl₃) |
| 97 | 3-Cl-4-CH₃O-C₆H₃— | COC(CH₃)₃ | CH₃ | CH₃ | O | Oil | 5.62 (CDCl₃) |
| 98 | 3-Cl-4-CH₃O-C₆H₃— | COCH₂Cl | CH₃ | CH₃ | O | Oil | 5.64 (CDCl₃) |
| 99 | 2-NO₂-3-Cl-C₆H₃— | COCH₂CH₂ | CH₃ | CH₃ | O | Oil; 1.5239 | 5.76 (CDCl₃) |
| 100 | 4-Cl-C₆H₄-O-C₆H₄— | CH₃ | CH₃ | CH₃ | O | Oil | 5.05 (CDCl₃) |
| 101 | 4-Cl-C₆H₄-O-C₆H₄— | CH(CH₃)₂ | CH₃ | CH₃ | O | Oil | 5.14 (CDCl₃) |
| 102 | 4-Cl-C₆H₄-O-C₆H₄— | CH(CH₃)₂ | CH₃ | CH₃ | S | Oil | 4.82 (CDCl₃) |
| 103 | 4-Cl-C₆H₄-O-C₆H₄— | CH₂CH₂Cl | CH₃ | CH₃ | O | Oil | 5.22 (CDCl₃) |
| 104 | 4-Cl-C₆H₄-O-C₆H₄— | COH | CH₃ | CH₃ | O | Oil | 5.68 (CDCl₃) |
| 105 | 4-Cl-C₆H₄-O-C₆H₄— | COCH₃ | CH₃ | CH₃ | O | Oil | 5.62 (CDCl₃) |
| 106 | 4-Cl-C₆H₄-O-C₆H₄— | COC(CH₃)₃ | CH₃ | CH₃ | O | Oil | 5.66 (CDCl₃) |
| 107 | C₄H₉-n | C₄H₉-n | CH₃ | CH₃ | S | Boiling point 112° C/0.01mm | 4.40 (CDCl₃) |
| 108 | C₄H₉-n | C₆H₅ | CH₃ | CH₃ | S | Boiling point 155–165° C .05mm | 4.73 (CDCl₃) |

TABLE 1-continued $$R-N(CH_2-X-R^1)-CO-N\langle{}^{R^2}_{R^3}\quad (I)$$

| Example No. | R | R¹ | R² | R³ | X | Melting point [° C]; Refractive index [$n_D^{20}$] | $\delta_{CH_2}$ (ppm) at 60 MHz TMS as internal standard (solvent) |
|---|---|---|---|---|---|---|---|
| 109 | Cl—C₆H₄— | COCH₃ | $C_4H_9$-n | $C_4H_9$-n | O | Oil; 1.5110 | 5.60 (CDCl₃) |
| 110 | Cl—C₆H₄— | CH₂—C≡CH | CH₂CH=CH₂ | CH₂—CH=CH₂ | O | Oil; 1.5611 | 5.14 (CDCl₃) |
| 111 | Cl—C₆H₄— | CO—C₆H₄—C(CH₃)₃ | CH₂CH=CH₂ | CH₂—CH=CH₂ | O | Oil; 1.5371 | 5.81 (CDCl₃) |
| 112 | Cl—C₆H₄— | CS—OC₂H₅ | CH₂—CH=CH₂ | CH₂—CH=CH₂ | S | Oil; 1.5756 | 5.35 (CDCl₃) |
| 113 | Cl—C₆H₄— | Cl—C₆H₄— | CH₂—CH=CH₂ | CH₂—CH=CH₂ | SO₂ | Oil; 1.5593 | 4.95 (CDCl₃) |
| 114 | Cl—C₆H₄— | (tetrahydropyranyl) *) | CH₂—CH=CH₂ | CH₂—CH=CH₂ | N | Oil; 1.5450 | 4.30 (CDCl₃) |
| 115 | Cl,Cl—C₆H₃— | (tetrahydropyranyl) *) | CH₂—CH=CH₂ | CH₂—CH=CH₂ | N | Oil; 1.5470 | 4.34 (CDCl₃) |
| 116 | Cl,Cl—C₆H₃— | COCH₃ | CH₂—CH=CH₂ | CH₂—CH=CH₂ | S | Oil; 1.5649 | 5.38 (CDCl₃) |
| 117 | Cl,Cl—C₆H₃— | COCCl₂CH₃ | CH₂—CH=CH₂ | CH₂—CH=CH₂ | O | Oil; 1.5458 | 5.75 (CDCl₃) |
| 118 | Cl,Cl—C₆H₃— | CO—cyclopropyl | CH₂—CH=CH₂ | CH₂—CH=CH₂ | O | Oil; 1.5478 | 5.58 (CDCl₃) |

The preparation of the starting materials (II) is illustrated in the following Examples.

EXAMPLE A

Preparation of 1-chloromethyl-1-phenyl-3,3-dimethylurea

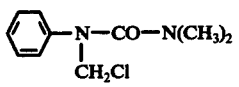

164 g (1 mole) of 1-phenyl-3,3-dimethylurea and 45 g (1.5 moles) of paraformaldehyde were suspended in 1,500 ml of anhydrous benzene. This suspension was saturated with dry hydrogen chloride gas by passing this gas in at a temperature of 10° C to 15° C. Thereafter 179 g (1.5 moles) of thionyl chloride were slowly added dropwise at a temperature of 15° to 20° C while stirring and cooling with ice.

After stirring overnight at room temperature, the solvent was distilled off in vacuo at 40° C bath temperature, with the exclusion of moisture. 100 ml of carbon tetrachloride were added to the residue, the mixture was filtered and the filtrate was distilled off in vacuo. The resulting oil was dried in a high vacuum.

212.5 g of 1-chloromethyl-1-phenyl-3,3-dimethylurea were obtained in quantitative yield. The compound was best characterized by its proton resonance spectrum (PMR): the chemical shift δ of the CH₂ group $$R-N(CH_2-Hal)-CO-N\langle{}^{R^2}_{R^3}\quad (IIa)$$

measured at 60 MHz in carbon tetrachloride as the solvent and against tetramethylsilane (TMS) (δ = 0 ppm) as the internal standard, was 5.58 ppm.

EXAMPLE B

Preparation of 3-(4-chlorophenyl)-3-chloromethyl-1,1-dimethylurea

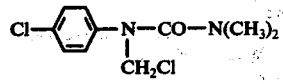

198.4 g (1 mole) of 3-(4-chlorophenyl)-1,1-dimethylurea were suspended in a solution of 33 g (1.1 moles) of paraformaldehyde in 1.5 l of anhydrous benzene. Dry hydrogen chloride gas was passed into this suspension for about 1 hour, while cooling with ice and stirring, in such a way that the internal temperature did not exceed 20° to 25° C. While passing in the gas, the suspension gradually became clear; solution occurred. 82.5 ml (1 mole) of thionyl chloride were then added dropwise to the solution obtained. While doing so, the temperature did not exceed 30° C.

After stirring for 12 hours, the solvent was distilled off in vacuo at 40° C external temperature, while excluding moisture. The residue was taken up in 250 ml of benzene and the benzene solution was freed of the unreacted starting urea by filtration. Thereafter the solvent of the filtrate was distilled off in vacuo.

237 g (96% of theory) of 3-(4-chlorophenyl)-3-chloromethyl-1,1-dimethylurea were obtained as an oil which crystallized on trituration with petroleum ether; melting point 37°–43° C; $\delta_{CH_2}$ = 5.49 ppm (measured at 60 MHz in CDCl$_3$, with TMS as the internal standard).

The compounds listed in Table 2 which follows were prepared by methods analogous to those described in Example a; they were also best characterized by the chemical shift ("δ - value" in ppm) of the newly formed —CH$_2$— group as a physico-chemical characteristic value.

Table 2

$$R-N(CH_2-Hal)-CO-N(R^2)(R^3) \quad (IIa)$$

| Example No. | R | R$^2$ | R$^3$ | Hal | δ-value (ppm), 60 MHz, TMS as internal standard (solvent) |
|---|---|---|---|---|---|
| c | 3,4-dichlorophenyl | OCH$_3$ | CH$_3$ | Cl | 5.46 (CCl$_4$) |
| d | 4-chlorophenyl | OCH$_3$ | CH$_3$ | Cl | 5.44 (CCl$_4$) |
| e | 3-chloro-4-trifluoromethoxyphenyl | CH$_3$ | CH$_3$ | Cl | 5.63 (CDCl$_3$) |
| f | 3-chloro-4-nitrophenyl | CH$_3$ | CH$_3$ | Cl | 5.61 (CDCl$_3$) |
| g | 3-chloro-4-methoxyphenyl | CH$_3$ | CH$_3$ | Cl | 5.56 (CDCl$_3$) |
| h | 4-ethylphenyl | CH$_3$ | CH$_3$ | Cl | 5.60 (CDCl$_3$) |
| i | 4-(4-chlorophenoxy)phenyl | CH$_3$ | CH$_3$ | Cl | 5.62 (CDCl$_3$) |
| j | 3,4-dichlorophenyl | CH$_3$ | CH$_3$ | Cl | 5.61 (CDCl$_3$) |
| k | 3,4-dichlorophenyl | CH$_3$ | C$_4$H$_9$-n | Cl | 5.58 (CDCl$_3$) |
| l | 4-chlorophenyl | C$_4$H$_9$-n | C$_4$H$_9$-n | Cl | 5.62 (CDCl$_3$) |
| m | 4-trifluoromethylphenyl | CH$_3$ | CH$_3$ | Cl | 5.74 (CDCl$_3$) |
| n | 4-methylphenyl | CH$_3$ | CH$_3$ | Cl | 5.59 (CDCl$_3$) |
| o | 3-methyl-4-chlorophenyl | CH$_3$ | CH$_3$ | Cl | 5.58 (CDCl$_3$) |
| p | 3,4-dichlorophenyl | morpholino (R$^2$+R$^3$) | | Cl | 5.58 (CDCl$_3$) |
| q | 3,4-dichlorophenyl | —CH$_2$—CH=CH$_2$ | —CH$_2$—CH=CH$_2$ | Cl | 5.59 (CDCl$_3$) |
| r | 4-chlorophenyl | —CH$_2$—CH=CH$_2$ | —CH$_2$—CH=CH$_2$ | Cl | 5.56 (CDCl$_3$) |
| s | C$_4$H$_9$-n | CH$_3$ | CH$_3$ | Cl | 5.16 (CDCl$_3$) |

The active compounds according to the invention have excellent herbicidal properties and can therefore be used for combating weeds.

Weeds in the broadest sense are plants which grow in places where they are not desired. As weeds there may be mentioned: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica), and groundsel (Senecio) and monocotyledons such as timothy (Phleum), bluegrass (Poa), fescue (Festuca), eleusine (Eleusine), foxtail (Setaria), ryegrass (Lolium) and barnyard grass (Echinochloa).

The active compounds according to the invention very greatly influence plant growth but in a different way, so that they can be used as selective herbicides.

They show particular advantages as selective herbicides in cultures of cotton, cereals and carrots. Some of the active compounds according to the invention can also be used advantageously as selective herbicidal agents in bean cultures. In high concentrations (above 10 kg/ha) the active compounds according to the invention are also suitable for the total combating of weeds.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clay, talc, chalk, quartz, attapulgite, montmorillonite or diatomaceous earth, or ground synthetic minerals, such as highly-dispersed silicic acid, alumina or silicates.

Preferred examples or emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds. The formulations generally contain from 0.1 to 95 percent by weight, preferably from 0.5 to 90 percent by weight, of active compound.

The active compounds can be used as such, in the form of their formulations or in the application forms prepared therefrom, such as ready-to-use solutions, emulsions, suspensions, powders, pastes and granules. They may be used in the customary manner, for example by watering, spraying, atomising, sprinkling and dusting.

They can be used both by the post-emergence process and by the pre-emergence process; they are preferably used after the emergence of the plants.

The amount of active compound employed can vary within fairly wide ranges; it depends essentially on the nature of the desired effect. In general, the amounts used are from 0.1 to 25 kg/ha, preferably from 0.5 to 10 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

In addition, the active compounds according to the invention show a fungitoxic and bactericidal activity and in particular they are active against sporulating fungi and blastomyces which attack both subterranean and above-ground parts of the plants, and also against fungi which attack rice, bananas and other crop plants. Their good activity against *Xanthomonas oryzae* should also be mentioned.

The herbicidal activity of the active compounds according to the invention is illustrated in the test Example which follows.

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Test plants, which had a height of 5–15 cm, were sprayed with the preparation of the active compound in such a way that the amounts of active compound per unit area indicated in the table was applied. Depending on the conconcentration of the spray liquor, the amount of water used between 1,000 and 2,000 1l/ha. After three weeks, the degree of damage to the plants was determined and characterised by the values 0–5, which had the following meaning:

0: no effect
1: a few slightly burnt spots
2: marked damage to leaves
3: some leaves and parts of stalks partially dead
4: plant partially destroyed
5: plant completely dead.

The active compounds, the amounts used and the results can be seen from the following table:

Table A

Post-emergence-Test

| Active compound | Amount of active compound, used kg/ha | Echinochloa | Chenopodium | Sinapis | Galinsoga | Stellaria | Urtica | Matricaria | Carrots | Oats | Cotton | Wheat | Beans |
|---|---|---|---|---|---|---|---|---|---|---|---|---|---|
| (33) 4-Cl-C$_6$H$_4$-N(CH$_2$-S-C$_4$H$_9$(n))-C(=O)-N(CH$_3$)$_2$ | 2 / 1 | 5 / 5 | 5 / 5 | 5 / 5 | 5 / 5 | 5 / 5 | 5 / 5 | 5 / 5 | 5 / 4 | 4-5 / 4 | 0 / 0 | 4 / 3 | 4-5 / 2 |
| (28) 4-Cl-C$_6$H$_4$-N(CH$_2$-S-CH$_3$)-C(=O)-N(CH$_3$)$_2$ | 2 / 1 | 5 / 5 | 5 / 4-5 | 5 / 5 | 5 / 5 | 5 / 5 | 5 / 5 | 5 / 5 | 5 / 4 | 4-5 / 2 | 0 / 0 | 4 / 3 | 4-5 / 2 |
| (5) 4-Cl-C$_6$H$_4$-N(CH$_2$-O-COC(CH$_3$)$_3$)-C(=O)-N(CH$_3$)$_2$ | 2 / 1 | 5 / 5 | 5 / 5 | 5 / 5 | 5 / 5 | 5 / 5 | 5 / 5 | 5 / 5 | 5 / 5 | 5 / 3 | 2 / 1 | 4 / 4 | 5 / 4-5 |
| (29) 4-Cl-C$_6$H$_4$-N(CH$_2$-O-CO-CH$_3$)-C(=O)-N(CH$_3$)$_2$ | 2 / 1 | 5 / 5 | 5 / 5 | 5 / 5 | 5 / 5 | 5 / 5 | 5 / 5 | 5 / 5 | 5 / 5 | 4-5 / 4 | 2 / 1 | 4-5 / 4 | 5 / 4 |
| (31) 4-Cl-C$_6$H$_4$-N(CH$_2$-O-CO-CH(CH$_3$)-CH$_3$)-C(=O)-N(CH$_3$)$_2$ | 2 / 1 | 5 / 5 | 5 / 5 | 5 / 5 | 5 / 5 | 5 / 5 | 5 / 5 | 5 / 5 | 5 / 5 | 4-5 / 4 | 2 / 1 | 4-5 / 4 | 5 / 5 |
| (2) C$_6$H$_5$-N(CH$_2$-O-CH$_3$)-C(=O)-N(CH$_3$)$_2$ | 2 / 1 | 5 / 5 | 5 / 5 | 5 / 5 | 5 / 4-5 | 5 / 5 | 5 / 5 | 5 / 5 | 5 / 5 | 4 / 4 | 0 / 0 | 4-5 / 3 | 5 / 3-4 |

Table A-continued
Post-emergence-Test

| Active compound | Amount of active compound, used kg/ha | Echinochloa | Chenopodium | Sinapis | Galinsoga | Stellaria | Urtica | Matricaria | Carrots | Oats | Cotton | Wheat | Beans |
|---|---|---|---|---|---|---|---|---|---|---|---|---|---|
| (40) $\begin{array}{c}\text{O} \\ \parallel \\ \text{N—C—N} \\ \text{CH}_2\text{—O—CO—C(CH}_3)_3 \end{array}$ (phenyl) CH$_3$/CH$_3$ | 2<br>1 | 5<br>5 | 5<br>4 | 5<br>5 | 5<br>4 | 5<br>4 | 5<br>5 | 4<br>4 | 5<br>3 | 4-5<br>3 | 0<br>0 | 3<br>2 | 3<br>2 |
| (41) $\begin{array}{c}\text{O} \\ \parallel \\ \text{N—C—N} \\ \text{CH}_2\text{—O—CO—CH=CH}_2 \end{array}$ (phenyl) CH$_3$/CH$_3$ | 2<br>1 | 5<br>5 | 5<br>5 | 5<br>5 | 5<br>4 | 5<br>3 | 5<br>5 | 5<br>4 | 5<br>4 | 4<br>3 | 2<br>1 | 2<br>2 | 2<br>0 |
| (26) $\begin{array}{c}\text{O} \\ \parallel \\ \text{N—C—N} \\ \text{CH}_2\text{—O—CO—CH}_3 \end{array}$ (3,4-diClPh) CH$_3$/OCH$_3$ | 2<br>1 | 5<br>5 | 5<br>5 | 5<br>5 | 5<br>5 | 5<br>5 | | 5<br>5 | 3<br>2 | 4-5<br>4 | 5<br>4-5 | 2<br>2 | 5<br>5 |
| (15) $\begin{array}{c}\text{O} \\ \parallel \\ \text{N—C—N} \\ \text{CH}_2\text{—O—CO—CH}_3 \end{array}$ (3,4-diClPh) CH$_3$/CH$_3$ | 2<br>1 | 5<br>5 | 5<br>5 | 5<br>5 | 5<br>5 | 5<br>5 | | | 5<br>5 | 5<br>5 | 4-5<br>4 | 3<br>3 | 3<br>2 | 5<br>5 |
| (17) $\begin{array}{c}\text{O} \\ \parallel \\ \text{N—C—N} \\ \text{CH}_2\text{—O—CO—C(CH}_3)_3 \end{array}$ (3,4-diClPh) CH$_3$/CH$_3$ | 2<br>1 | 5<br>4 | 5<br>4-5 | 5<br>5 | 5<br>5 | 5<br>5 | 5<br>4 | 3<br>2 | 1<br>0 | 4-5<br>2 | 3<br>2 | 3<br>2 | 5<br>5 |
| (102) $\begin{array}{c}\text{O} \\ \parallel \\ \text{N—C—N} \\ \text{CH}_2\text{—O—CH(CH}_3)_2 \end{array}$ (3-Cl-4-OCH$_3$Ph) CH$_3$/CH(CH$_3$)$_2$ | 2<br>1 | | | 5<br>5 | | | | | | 4-5<br>4 | 2<br>1 | 2<br>1 | 5<br>5 |

Table A-continued
Post-emergence-Test

| Active compound | Amount of active compound, used kg/ha | Echinochloa | Chenopodium | Sinapis | Galinsoga | Stellaria | Urtica | Matricaria | Carrots | Oats | Cotton | Wheat | Beans |
|---|---|---|---|---|---|---|---|---|---|---|---|---|---|
| CH$_3$—O—⟨phenyl-Cl⟩—N(—C(=O)—N(CH$_3$)$_2$)(CH$_2$—O—CHO) (105) | 2<br>1 | 5<br>4 | 5<br>4 | 5<br>5 | 5<br>5 | 5<br>5 | 5<br>5 | 5<br>4 | 1<br>0 | 4-5<br>3 | 3<br>2 | 2<br>0 | 4-5<br>4-5 |
| CH$_3$—O—⟨phenyl-Cl⟩—N(—C(=O)—N(CH$_3$)$_2$)(CH$_2$—O—CO—C(CH$_3$)$_3$) (107) | 2<br>1 | 5<br>5 | 5<br>5 | 5<br>5 | 5<br>5 | 5<br>5 | 5<br>5 | 5<br>5 | 1<br>0 | 4-5<br>3 | 3<br>2 | 1<br>0 | 5<br>4 |
| Cl—⟨phenyl⟩—NH—CO—N(CH$_3$)$_2$ (known) | 2<br>1 | 5<br>5 | 5<br>5 | 5<br>5 | 5<br>5 | 5<br>5 | 5<br>5 | 5<br>5 | 5<br>5 | 4-5<br>4 | 3<br>2 | | 5<br>4-5 |
| Cl—⟨phenyl-Cl⟩—NH—CO—N(CH$_3$)$_2$ (known) | 2<br>1 | 5<br>5 | 5<br>5 | 5<br>5 | 5<br>5 | 5<br>5 | 5<br>5 | 5<br>5 | 5<br>5 | 4<br>4 | 4<br>2 | 3<br>2 | 5<br>5 |
| Cl—⟨phenyl-Cl⟩—NH—CO—N(OCH$_3$)(CH$_3$) (known) | 2<br>1 | | | 5<br>5 | 5<br>5 | 5<br>5 | 5<br>5 | 5<br>5 | 5<br>3 | 4-5<br>4 | 5<br>5 | 3<br>2 | 5<br>5 |

It will be understood that the specification and examples are illustrative but not limitative of the present invention and that other embodiments within the spirit and scope of the invention will suggest themselves to those skilled in the art.

What is claimed is:

1. N,N'-tetrasubstituted urea compound of the formula

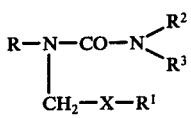

wherein
X is oxygen
R is alkyl of from 1 to 4 carbon atoms, phenyl, benzyl or substituted phenyl or benzyl wherein the substitutent is at least one of halogen, alkyl of from 1 to 4 carbon atoms, alkoxy of from 1 to 4 carbon atoms, haloalkoxy of from 1 to 5 halo atoms, phenoxy, halophenoxy and nitrophenoxy;
$R^1$ is —C(Y)-$R^4$ wherein Y is oxygen and $R^4$ is alkyl, alkenyl, alkynyl, alkoxyalkyl, haloalkyl, haloalkynyl, cycloalkyl or cycloalkenyl of from 3 to 8 ring carbons and wherein $R^4$ contains not more than 11 carbon atoms; or is hydrogen or alkyl substituted by alkoxy and alkoxycarbonyl,
$R^2$ is alkyl, substituted alkyl, alkenyl, substituted alkynyl, wherein the substituents are at least one of alkoxy of from one to three carbon atoms, haloalkyl of from one to two carbon atoms and one to three halogen atoms, and halogen, alkoxy or cycloalkyl of from 3 to 8 ring carbon atoms;
$R^3$ is alkyl, haloalkyl or alkenyl of up to 4 carbon atoms;
$R^2$ and $R^3$ represent an alkylene bridge.

2. Compound as claimed in claim 1 wherein $R^4$ is alkyl, or haloalkyl.

3. Compound as claimed in claim 1 wherein $R^1$ is alkenyl or alkynyl.

4. Compound as claimed in claim 1 wherein $R^1$ is alkoxyalkyl.

5. Compound as claimed in claim 1 wherein $R^1$ is cycloalkyl, or cycloalkenyl.

6. Compound as claimed in claim 1 wherein R is phenyl substituted with at least one halogen atom.

7. Compound as claimed in claim 1 wherein $R^2$ is straight-chain or branched alkyl of from 1 to 4 carbon atoms or alkenyl of from 2 to 6 carbon atoms, either of which can be substituted by at least one of: alkoxy of from 1 to 3 carbon atoms, haloalkyl of from 1 to 2 carbon atoms and 1 to 3 halogen atoms or halogen, or $R^2$ is alkoxy of from 1 to 4 carbon atoms.

8. Compound as claimed in claim 1 wherein $R^3$ is straight-chain or branched alkyl of from 1 to 4 carbon atoms, which can be mono-substituted or poly-substituted by halogen, or is alkenyl of from 2 to 6 carbon atoms.

9. Compound as claimed in claim 1 wherein $R^2$ and $R^3$ together form a straight-chain or branched alkylene bridge of from 3 to 8 ring atoms, forming a heterocyclic ring with the adjoining nitrogen atom.

10. Compound as claimed in claim 2 wherein $R^4$ is hydrogen, straight-chain or branched alkyl or haloalkyl of from 1 to 6 carbon atoms, the latter having 1 to 3 halogen atoms, or substituted alkyl of 1 to 2 carbon atoms, the substituent being at least one of alkoxy or alkoxycarbonyl from 1 to 3 carbon atoms in the alkyl moiety, or $R^4$ is straight-chain or branched alkenyl or haloalkenyl of from 2 to 6 carbon atoms and from 1 to 4 halogen atoms, straight-chain or branched alkynyl or haloalkynyl of from 3 to 6 carbon atoms and from 1 to 4 fluorine or chlorine atoms, or cycloalkyl or cycloalkenyl of from, in either case, 3 to 8 ring carbon atoms.

11. Compound as claimed in claim 1 designated 3-(3,4-dichlorophenyl)-3-(tert.-butyl-1-carboxymethyl)-1,1-dimethyl urea of the formula

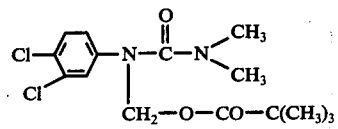

12. Compound as claimed in claim 1 designated 3-(3,4-dichlorophenyl)-3-(methyl-carboxymethyl)-1-methyl-1-methoxy urea of the formula

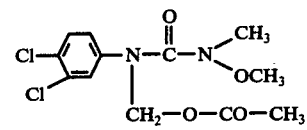

13. Compound as claimed in claim 1 designated 3-(4-chlorophenyl)-3-(isopropyl-1-carboxymethyl)-1,1-dimethyl urea of the formula

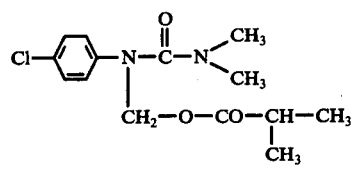

14. Compound as claimed in claim 1 designated 3-phenyl-3-(tert.butyl-1-carboxymethyl)-1,1-dimethyl urea of the formula

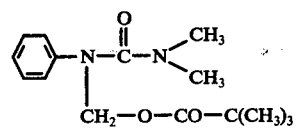

15. Herbicidal composition comprising a herbicidally acceptable carrier and, in effective amounts, an N,N'-tetrasubstituted urea compound as claimed in claim 1.

16. Method of combatting undesired vegetation, which method comprises applying to such vegetation or to its habitat, herbicidally effective amounts of an N,N'-tetrasubstituted urea compound of the formula

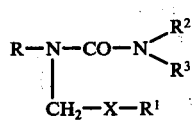

wherein
X is oxygen
R is alkyl of from 1 to 4 carbon atoms, phenyl, benzyl or substituted phenyl or benzyl wherein the substitutent is at least one of halogen, alkyl of from 1 to 4 carbon atoms, alkoxy of from 1 to 4 carbon atoms, haloalkoxy of from 1 to 5 halo atoms, phenoxy, halophenoxy and nitrophenoxy;

$R^1$ is —C(Y)-$R^4$ wherein Y is oxygen and $R^4$ is alkyl, alkenyl, alkynyl, alkoxyalkyl, haloalkyl, haloalkynyl, cycloalkyl or cycloalkenyl of from 3 to 8 ring carbons; or is hydrogen or alkyl substituted by alkoxy and alkoxycarbonyl, $R^2$ is alkyl, substituted alkyl, alkenyl, substituted alkynyl, wherein the substituents are at least one of alkoxy of from one to three carbon atoms, haloalkyl of from one to two carbon atoms and one to three halogen atoms, and halogen, alkoxy or cycloalkyl of from 3 to 8 carbon atoms;

$R^3$ is alkyl, haloalkyl or alkenyl or up to 4 carbon atoms;

$R^2$ and $R^3$ represent an alkylene bridge.

17. Method as claimed in claim 16 wherein said compound is selected from the group consisting of
- 3-(3,4-dichlorophenyl)-3-(tert. butyl-1-carboxymethyl)-1,1-dimethyl urea
- 3-(3,4-dichlorophenyl)-3-(methyl-carboxymethyl)-1-methyl-1-methoxy urea
- 3-(4-chlorophenyl)-3-(isopropyl-1-carboxymethyl)-1,1-dimethyl urea, and
- 3-phenyl-3-(tert. butyl-1-carboxymethyl)-1,1-dimethyl urea.

18. Method as claimed in claim 16 wherein said compound is applied to weeds or their habitat growing in a crop cultivation to selectively injure the weeds without substantial damage to the crops.

19. Method as claimed in claim 18 wherein said crop cultivation is of cotton, cereals, carrots or beans.

* * * * *